United States Patent [19]

Day et al.

[11] Patent Number: 5,229,277
[45] Date of Patent: Jul. 20, 1993

[54] PROCESS FOR THE PRODUCTION OF DEXTRAN POLYMERS OF CONTROLLED MOLECULAR SIZE AND MOLECULAR SIZE DISTRIBUTIONS

[75] Inventors: Donal F. Day; Doman Kim, both of Baton Rouge, La.

[73] Assignee: Louisiana State University Board of Supervisors, Baton Rouge, La.

[21] Appl. No.: 664,755

[22] Filed: Mar. 5, 1991

[51] Int. Cl.$^5$ .............................................. C12P 19/08
[52] U.S. Cl. ..................................... 435/103; 435/211
[58] Field of Search ............................. 435/103, 211

[56] References Cited

U.S. PATENT DOCUMENTS

| | | | |
|---|---|---|---|
| 4,487,831 | 12/1984 | Day et al. | 435/99 |
| 4,732,854 | 3/1988 | Day et al. | 435/211 |
| 4,820,640 | 4/1989 | Day et al. | 435/211 |

FOREIGN PATENT DOCUMENTS 653066 11/1962 Canada .

Primary Examiner—Ronald W. Griffin
Assistant Examiner—Pamela S. Webber
Attorney, Agent, or Firm—Llewellyn A. Proctor

[57] ABSTRACT

A process for the production of dextran polymers of controlled average number molecular weight sizes, and molecular weight size distributions via the mixed culture fermentation of *Leuconostoc mesenteroides* and a constitutive mutant microorganism capable of elaborating the enzyme dextranase, particularly *Lipomyces starkeyi* ATCC 74054, in the presence of sucrose. The *Leuconostoc mesenteroides* produces the dextran polymer, and the mutant *Lipomyces starkeyi* ATCC 74054 concurrently produces dextranase, an enzyme whose activity reduces the size of the dextran polymers and permits their growth or reduction in molecular weight size in direct relation to the temperature and time period regimen imposed as conditions for the reactions.

19 Claims, No Drawings

PROCESS FOR THE PRODUCTION OF DEXTRAN POLYMERS OF CONTROLLED MOLECULAR SIZE AND MOLECULAR SIZE DISTRIBUTIONS

FIELD OF THE INVENTION

This invention relates to a process for the production of dextran polymers, or dextran, of controlled molecular size. In particular, it relates to a process for the mixed culture fermentation of *Leuconostoc mesenteroides*, and a mutant *Lipomyces starkeyi* ATCC 74054 to produce dextran polymers of controlled molecular sizes, and narrow molecular size distributions.

BACKGROUND

The production of dextran is known. Interest in dextran polymers began largely in view of their potential for use in various food products as conditioners, stabilizers, "bodying agents" or related uses in which they would replace natural gums. The term "dextran" collectively describes a large class of bacterial extracellular hydrocolloid homopolysaccharides consisting of alpha-D-glucopyranosyl units polymerized predominantly in an alpha, 1→6 linkage. Dextran is synthesized from sucrose catalyzed by dextransucrose (sucrose: 1,6-alpha-D-glucan 6-alpha-glucosyltransferase EC 2.4.1.5). Thus, the dextransucrase enzyme catalyzes the synthesis of dextran via the reaction: sucrose→dextran+fructose. Hydrolysis of the sucrose provides the energy required for the condensation of D-glucopyranosyl units. The reaction can be carried out in vitro, without energy or cofactors, using only purified enzyme and sucrose.

Many different species of the genera Leuconostoc, and other bacteria, are known to synthesize dextran polymers from sucrose, e.g. *Leuconostoc mesenteroides*, e.g. the strain NRRL B-512 (F) or ATCC 10830. Sucrose induces the formation of dextransucrase in the organism *Leuconostoc mesenteroides*. It is reported by Donald E. Brown and Alexander McAvoy "A pH-Controlled Fed-Batch Process for Dextransucrose Production," *J. Chem. Tech. Biotechnol.* 1990, 48, 405–414, that a commercial dextran is commonly produced by the bacterium *Leuconostoc mesenteroides* strain NRRL B-512-F which contains 95% of 1,6- and 5% of 1,3-D glucopyranosidic linkages, and that most of the dextran is marketed as either blood volume expander or flow improver with the means of their molecular weight distributions at 70,000 and 40,000 respectively.

Certain strains of yeast, notably strains of *Lipomyces starkeyi*, are known to have dextranase activity. Whereas most strains of this organism have not been considered for the commercial production of dextranase because of its slow growth, and the difficulty of avoiding contamination from other organisms during growth, *Lipomyces starkeyi* ATCC No. 12659 has been used to hyperproduce extracellular dextranase at lesser lag time when cultured at pH ranging about 2.5 to 4.5 in an aqueous nutrient medium containing nitrogen and mineral sources, and an assimilable carbon source for growth and energy ... viz. a dextranase inducer, suitably dextran, or glucose. This process, organism and a method for the production of this organism from a parent strain, *Lipomyces starkeyi* ATCC No. 20825, a less dextranase-active species per se, are described by reference to U.S. Pat. No. 4,732,854 which issued Mar. 22, 1988 to Donal F. Day et al.

The dextran that is produced by current technology is of relatively high molecular weight, and the molecular weight range distribution is quite wide. Thus, e.g., the best current technology for dextran products consists in producing dextran by fermentation with sucrose with *Leuconostoc mesenteroides*, separating the polymer by alcohol precipitation, conducting enzymatic or acidic hydrolysis of the polymer, and then chromatographically separating the polymer into the desired fractions. The product yields have a high polydispersity index. To obtain dextran polymers of a more select, narrower molecular weight range distribution, e.g. a polydispersity index of about 1 or 2, additional processing steps are required, e.g. enzymatic hydrolysis and chromatographic separation steps. This, of course, adds to the costs of producing polymers of preselected, narrow molecular weight range distribution as is required in the production of many dextran polymer products, e.g. blood plasma. Thus, a better process is needed for this purpose.

OBJECTS

It is, accordingly, a primary objective of this invention to provide a process for the production of high purity dextran polymers of more uniform molecular weight range distribution; particularly dextran polymers of relatively low number average molecular weight.

A specific object is to provide a process for the mixed culture fermentation, with microorganisms, to produce high purity dextran polymers of controlled, preselected molecular size, and narrow molecular size distributions.

A further, and more specific object is to provide a mixed culture fermentation process for the production from sucrose of dextran polymers of desired, preselected average molecular weight, with a polydispersity index of about 1.

A further, and yet more specific object is to provide a mixed culture fermentation process, as characterized, for the direct production from sucrose of high quality dextran polymers suitable for use as blood plasma, or blood plasma extender, without any requirement for further separation and grading of the polymers to obtain different molecular weight size distributions.

THE INVENTION

These objects and others are achieved in accordance with the present invention which embodies a process wherein cultures of (i) *Leuconostoc mesenteroides*, a species of bacteria, preferably grown to a stationary phase in a fermentation medium, and (ii) a constitutive mutant microorganism capable of elaborating dextranase in the presence of sucrose, or glucose, preferably *Lipomyces starkeyi* ATCC 74054, a species of yeast, preferably grown to a stationary phase in a fermentation medium, are admixed one with the other in a single production fermentation medium and cultivated in the presence of sucrose to produce dextran polymers. The *Leuconostoc mesenteroides*, in this reaction as in known reactions, produces dextransucrase. The sucrose that is present, or added in excess beyond the growth requirement of the microorganisms is converted into dextran by the dextransucrase that is produced. On the other hand, the constitutive mutant microorganism, notably and preferably *Lipomyces starkeyi* ATCC 74054, elaborates dextranase which reacts with, and reduces the molecular size of the dextran polymers as they are formed. The dextran polymers, beginning as polymers of relatively low average molecular weight, and narrow molecular weight size distribution, can then be grown by carefully controlling conditions of the process to a desired preselected average molecular weight, with continued narrow molecular weight size distribution. Conversely, dextran polymers of relatively high average molecular weight if such were produced can be reduced in average molecular weight size, and molecular weight distribution by action of the dextranase. Thus, unlike earlier processes for the production from sucrose of dextran from *Leuconostoc mesenteroides* alone, the use of both *Leuconostoc mesenteroides* and a constitutive mutant microorganism capable of elaborating dextranase, notably *Lipomyces starkeyi* ATCC 74054, provide a means for realistic control during the synthesis to grow, from dextran polymers of low average molecular weight, narrow range distribution, polymers of desired, preselected average molecular weight, with continued narrow molecular weight size distribution.

The production from sucrose of dextran polymers in the single fermentation medium via use of the mixed culture makes it feasible to produce high quality, low polydispersity dextran of desired preselected molecular size. Starting with dextran of low average molecular weight, due to the action of the dextranase, the dextran polymer can then be grown in the process to a desired, preselected average molecular weight having a low polydispersity index by careful control of the fermentation time, temperature, pH, and aeration, or combination of these conditions. This process in effect eliminates the enzymatic or acidic hydrolysis and chromatographic separation steps presently employed in the *Leuconostoc mesenteroides* process to produce dextran polymers, increases the flexibility of the polymer production system, and produces a wider range of products of higher quality for various uses.

The mixed cultures required for the practice of this invention are obtained from inocula prepared by the separate fermentation of (i) *Leuconostoc mesenteroides*, Leuconostoc being a well known genera of bacteria of which *Leuconostoc mesenteroides* is a commonly known species, and (ii) a constitutive mutant microorganism capable of elaborating dextranase in the presence of sucrose, or glucose, preferably *Lipomyces starkeyi* ATCC 74054, a mutant of the genera of yeast of the family Lipomyces, respectively. *Leuconostoc mesenteroides*, of which *Leuconostoc mesenteroides* i.e. the strain NRRL B-512(F) or ATCC 10830 is typical, well known and available, is readily cultivated by growing to a stationary phase in an aqueous medium at temperature ranging from about 20° C. to 40° C., suitably about 30° C., at pH ranging about 4.5 to 6.5, suitably about 5.7, in standard media; suitably one containing a yeast extract, peptone, phosphate buffer, glucose starter or other assimilable carbon source, and minerals. *Leuconostoc mesenteroides*, grown to a stationary phase, is generally present in an inoculum in concentration ranging from about 0.1 mg/ml to about 20.0 mg/ml, suitably about 4 mg/ml. The fermentation broth can be used directly for admixing with the (ii) constitutive mutant microorganism which is capable of elaborating dextranase, preferably *Lipomyces starkeyi* ATCC 74054.

*Lipomyces starkeyi* ATCC 74054 is obtained by a mutation of a yeast of the family Lipomyces, this microorganism having been found capable of elaborating dextranase when added to a fermentation medium and cultivated in the presence of sucrose. *Lipomyces starkeyi* ATCC 74054 is produced by selecting a Lipomyces microorganism, e.g. *Lipomyces starkeyi (ATCC* 12659), growing the colony of microorganisms in nitrosoguanidine (NTG), selecting the surviving microorganisms which can produce dextranase using glucose, sucrose, maltose, starch, dextran and the like as an energy source, and cultivating the microorganisms to obtain said *Lipomyces starkeyi* ATCC 74054.

The mutant *Lipomyces starkeyi* ATCC 74054, as a genera of yeast of the family Lipomyces appears unique in its ability to elaborate dextranase when cultivated in a fermentation medium in the presence of sucrose. No other species of Lipomyces, insofar as known, possesses this characteristic. For example, the organism of the family *Lipomyces starkeyi* 12659, from which *Lipomyces starkeyi* ATCC 74054 was prepared, does not possess this property. *Lipomyces starkeyi* ATCC 74054, after isolation however, can be readily cultivated and grown in an aqueous fermentation medium in much the same manner as *Leuconostoc mesenteroides* for forming an inoculum of the microorganism for admixture with the latter. *Lipomyces starkeyi* ATCC 74054 can thus be cultivated by growing, preferably to a stationary phase, in an aqueous medium at temperature ranging from about 20° C. to 40° C., suitably about 30° C., at pH ranging from about 2.5 to 8, suitably about 4, in a standard media, or medium containing a yeast extract peptone, phosphate buffer, sucrose starter or other assimilable carbon source, and minerals. *Lipomyces starkeyi* ATCC 74054, grown to a stationary phase, is generally present in an inoculum in concentration ranging from about 0.5 mg/ml to about 70 mg/ml, suitably about 14 mg/ml. The fermentation broth can be used directly for admixing with *Leuconostoc mesenteroides*.

A deposit of the mutant microorganism *Lipomyces starkeyi* ATCC 74054 has been made with the American Type Culture Collection, at 12301 Parklawn Drive, Rockville, Md. 20852. The microorganism, as parenthetically indicated, has been given an identifying number, 74054. The microorganism, on patenting, will be maintained on deposit for a period of thirty years, for five years after the last request for the microorganism, or for the enforceable life of the patent, whichever is longer. Should the deposit become nonviable it will be replaced. Assurance of access to the deposit as determined by the commissioner under 37 CFR 1.14 is provided for. All restrictions on the availability of a deposit to the public will be irrevocably removed on the granting of a patent.

In initiating the process of this invention, or at startup, an inoculum of (i) *Leuconostoc mesenteroides*, grown to a stationary phase in an aqueous fermentation medium, and an inoculum of (ii) *Lipomyces starkeyi* ATCC 74054 or other constitutive mutant microorganism capable of elaborating dextranase, grown to a stationary phase in an aqueous fermentation medium, are admixed one with the other and inocula charged into a single fermentation vessel; or charged into a single fermentation vessel and admixed therein. The ratio and proportions of the admixture formed is such that the *Leuconostoc mesenteroides* will form dextran from the sucrose that is present in the added inoculum, or added sucrose; and such that the *Lipomyces starkeyi* ATCC 74054, or other dextrase elaborating mutant microorganism, will form dextranase. Suitably, the inoculum of *Lipomyces starkeyi* ATCC 74054 and *Leuconostoc mesenteroides* (ATCC 10830), respectively, are admixed together in a volume ratio of *Lipomyces starkeyi* ATCC 74054:*Leuconostoc mesenteroides* ranging from about 1:10 to about 10:1, preferably from about 1:1 to about 10:1, with a 5:1 ratio of the two inocula having been found quite satisfactory. The fermentation vessel is also charged with a standard salt solution, i.e. yeast extract, peptone, sucrose or glucose starter, and minerals as is conventional in the production of dextran polymers from sucrose with *Leuconostoc mesenteroides*. Sucrose must be present to initiate production, generally in concentration ranging from about 0.2 to about 50%; optimally about 20%. In the preferred method of operation, the fermentation vessel is operated as a modified fed-batch. Sucrose is added intermittently in a first step of the operating phase to the fermentation vessel, after consumption of the initial carbon source sufficient to maintain, during the first step of the operating phase, a sucrose concentration within a range of from about 1% to about 3%, preferably about 1.5% to about 2.5%, based on the weight of the fermentation broth. The process also requires aeration, air being introduced at a rate generally between about 0.5 v/v (volume air:-volume liquid) and about 5.0 v/v, about 1 v/v generally being about optimum. The fermentation is continued at temperature ranging from about 15° C. to about 30° C., preferably from about 25° C. to about 28° C., at pH ranging from about 4.0 to about 7.0, preferably from about 5.0 to about 5.3, until the dextran polymers have grown to the desired particle size; this generally requiring from about 7 hours to about 22 hours. At the end of this period, the temperature is preferably increased to that which is about optimum for formation of the dextranase, additional sucrose is added, and the reaction is continued.

At the beginning of the second step of the operation, after the temperature is increased, the balance of the sucrose to be converted to dextran, based on the stoichiometry of the reaction, may be charged in bulk to the fermentation vessel and the reaction continued, suitably at the higher temperature level until all of the sucrose has been consumed and converted into dextran polymer of the desired molecular size. The second step of the operation generally requires an additional period of time ranging from about 12 hours to about 48 hours at temperature ranging from about 25° C. to about 35° C., or preferably from about 32 hours to about 38 hours, at temperature ranging from about 28° C. to about 30° C. The dextran polymer, typically about 58 hours after the operation was begun, is then harvested by conventional means. Suitably, this is done by centrifugation, with ethanol precipitation of the dextran polymer.

Dextran polymers of average number molecular weight size ranging from about 70,000 to 75,000, with a polydispersity index of about 2 have been found commercially useful for the production of blood plasma, or blood plasma extender. This product has been made by producing high molecular weight dextran by fermentation of sucrose with *Leuconostoc mesenteroides*, separation of the polymer by alcohol precipitation, and thereafter conducting enzymatic or acidic hydrolysis of the polymer, and chromatographically separating out the desired fractions. However, a higher purity dextran polymer having a lower polydispersity index of about 1 can be made, and made more efficiently, via the direct use of the process of this invention, without any necessity of enzymatic or acidic hydrolysis of the polymer, or chromatographic separation steps.

Dextran polymers of desired, preselected average number molecular weight size within the ranges of from about 40,000 to about 150,000, preferably from about 70,000 to about 100,000, having a polydispersity index of about 1, can be readily directly made via the process of this invention. The molecular size of the dextran polymers produced can be preselected at will simply by selection of the period of time required for the fermentation, or temperature, or combination of the period of time required for the fermentation and temperature. Temperature control is necessary to regulate both the growth of the *Lipomyces starkeyi* ATCC 74054 and the *Leuconostoc mesenteroides*, and as well the activity and stability of both the dextranase and dextransucrase. The relationship between temperature and time ideally, for the different stages of operation, can be expressed as follows:

Stage 1. During this stage the growth optimum for *Leuconostoc mesenteroides* is 30° C. but the stability of the dextransucrase is decreased at this temperature. In order to balance the constraints of maximum *Leuconostoc* growth and decreased dextransucrase stability this phase is operated at about 28° C.

The length of time of this stage is dependant upon the initial sucrose concentration and the operating temperature. The length of this first stage proceeds until the residual sucrose concentration in the fermentation is less than 0.01%. At 28° C. with a 2% sucrose starting concentration this stage is about 10 hours. At less than 28° C. with the same carbon source the time period is 20 hours or greater.

Stage 2. The time of operation is critical at this stage for dextran size control. The temperature is increased in order to increase the rate of dextransucrase activity. The fermentation medium during this stage, because it now contains some dextran, acts to stabilize the dextransucrase to the higher temperatures.

The following is a tabulation of average molecular weight (size) vs. time in hours after the second sucrose addition, to wit:

| Time After Second Addition Of Sucrose, Hours | Molecular Weight, × 1000 |
|---|---|
| 20 | 150 |
| 36 | 77 |
| 39 | 68.7 |
| 42 | 100 |
| 44 | 42 |

The following is a tabulation demonstrating the efficiency of the process. In the tabulation, dextran production is given as a percent of theoretical yield. The percent theoretical yield is given for different periods of time following the second addition of sucrose.

| Time After Second Addition Of Sucrose, Hours | % Theoretical Yield |
|---|---|
| 20 | 90 |
| 36 | 92 |
| 39 | 90 |
| 42 | 90 |
| 44 | 79 |

These data stand in sharp contrast with the efficiency of a process for the production of dextran, as presently employed: typically 66% of theoretical yield.

The following is a tabulation of polydispersity vs. time after the second addition of sucrose.

| Time After Second Addition Of Sucrose, Hours | Polydispersity Index |
| --- | --- |
| 20 | 1.2 |
| 36 | 1.27 |
| 39 | 1.14 |
| 42 | 1.2 |
| 44 | 1.18 |

This process is more efficient than the existing commercial process. The commercial process does not normally use more than 15% sucrose. In contrast however, the process of this invention can utilize 20 wt. % or higher sucrose with the addition of a third stage.

The following is exemplary of a three stage operation using 20 wt. % sucrose.

|  | Stage 1 | Stage 2 | Stage 3 |
| --- | --- | --- | --- |
| Temp °C. | 28 | 28–30 | 30 |
| pH | 6.0–5.4 | 5.3–5.1 | 5.3–5.1 |
| Sucrose wt. % | 2.0 | 14.0 | 4.0 |
| Aeration v/v | 2 | 1 | 1 |
| Agitation rpm | 75–100 | 50 | 50 |

The following non-limiting example is further exemplary of such process. In the example percentages and parts are expressed in terms of weight units, and temperature is given in Centigrade degrees, unless otherwise expressed.

EXAMPLE

Inocula for the two cultures were separately started:

A *Leuconostoc mesenteroides* B-512 culture was started on a 2% glucose solution, at pH 5.8 and 30° C.

A *Lipomyces starkeyi* ATCC 74054 culture was grown on a 5% sucrose solution, at pH 4.3 and 30° C.

The inocula on reaching a stationary stage were blended together in a single fermentation vessel containing a 2.3% sucrose solution to start the production fermentation. The inocula added to the production vessel consisted of a 1% solution of *Leuconostoc mesenteroides* and 5% of the *Lipomyces starkeyi* ATCC 74054 cultures to the total production volume. The reaction medium was maintained at pH 5.8 and a temperature of 28° C., while the sucrose concentration of the fermentation broth was maintained at a level of 2.3%. After operation of these conditions for a period of 12 hours, the culture was then operated as a modified fed-batch with a single addition of sucrose sufficient to make a final sucrose concentration of 20%, based on the weight of the fermentation broth. The temperature was increased to 30° C. to increase dextranase activity, and the fermentation was then allowed to proceed for an additional 36 hours, at which time dextran of the desired molecular weight size had been produced. Variation of the length of time of this second stage, at the selected conditions of operation, controls the molecular size, and molecular size distribution of the dextran that is produced.

The dextran polymer was then isolated from the fermentation broth by ethanol precipitation, and centrifugation. Analysis of the dextran product shows a polydispersity index of approximately 1 for the overall production.

Various modifications and changes can be made, as will be apparent to those skilled in this art, without departing the spirit and scope of the invention.

Having described the invention, what is claimed is:

1. A process for the production from sucrose of dextran polymers within a range of controlled number average molecular weight sizes, and molecular size distributions, which comprises cultivating in the presence of sucrose in a single production fermentation reaction zone a mixture of the microorganism *Leuconostoc mesenteroides* and a constitutive mutant microorganism which produces the enzyme dextranase in said fermentation reaction while in the presence of said sucrose, imposing a temperature and time period regimen sufficient that the activity of the enzyme reduces the molecular size of the dextran polymers and permit their growth in direct relation to the imposed temperature and time period.

2. The process of claim 1 wherein the constitutive mutant microorganism of the mixture of microorganisms is one having all of the identifying characteristics of *Lipomyces starkeyi* ATCC 74054.

3. The process of claim 1 wherein the *Leuconostoc mesenteroides* is a microorganism having all of the identifying characteristics of *Leuconostoc mesenteroides* ATCC 10830.

4. The process of claim 1 wherein the *Leuconostoc mesenteroides* is a microorganism having all of the identifying characteristics of *Leuconostoc mesenteroides* ATCC 10830, and the constitutive mutant microorganism of the mixture of microorganisms is one having all of the identifying characteristics of *Lipomyces starkeyi* ATCC 74054.

5. The process of claim 1 wherein each of the microorganisms of the mixture is obtained from a fermentation medium wherein the respective microorganism is grown to a stationary phase prior to their addition to the production fermentation reaction zone.

6. The process of claim 5 wherein the microorganisms are admixed one with the other and cultivated within the production fermentation reaction zone in two discrete stages, a first stage at pH, temperature and period length sufficient to produce dextran polymer and dextranase in high concentrations, a second stage wherein the temperature is raised to increase the activity of the dextranase, the reaction being continued for a period of time at said temperature to produce a dextran polymer of controlled number average molecular weight size, and then harvesting the dextran polymer.

7. The process of claim 6 wherein the regimen of conditions imposed on the production fermentation reaction zone during the two discrete stages ranges as follows:

|  | In the first stage: | In the second stage: |
| --- | --- | --- |
| Range Temperature, °C.: | about 15 to 30 | about 25 to 35 |
| Range pH: | about 4 to 7 | about 4 to 7 |
| Time period range, hours: | about 5 to 30 | about 12 to 48. |

8. The process of claim 7 wherein the regimen of conditions imposed on the production fermentation reaction zone during the two discrete stages ranges as follows:

|  | In the first stage: | In the second stage: |
| --- | --- | --- |
| Range Temperature, °C.: | about 25 to 28 | about 28 to 30 |
| Range pH: | about 5.4 to 6.0 | about 5.0 to 5.3 |

-continued

| | In the first stage: | In the second stage: |
|---|---|---|
| Time period range, hours: | about 10 to 25 | about 32 to 38. |

9. The process of claim 8 wherein the number average molecular weight of the dextran polymer ranges from about 70,000 to about 75,000, and has a polydispersity index of about 1.

10. The process of claim 9 wherein the dextran polymer is of high purity and suitable as a blood plasma, or blood plasma extender after isolation from the production fermentation reaction zone.

11. A process for the production of dextran polymers within a range of controlled number average molecular weight sizes, and molecular size distributions, which comprises
cultivating in a single production fermentation zone a mixture of
  (i) the microorganism *Leuconostoc mesenteroides*, sufficient to grow dextran polymers, and
  (ii) a microorganism having all of the identifying characteristics of *Lipomyces starkeyi* ATCC 74054, sufficient to produce dextranase,
adding sucrose to the production fermentation zone during a first stage to an initial sucrose concentration level in said zone within a range of from about 1 percent to about 3 percent, based on the weight of the fermentation medium, maintaining the pH within a range of from about 4.0 to about 7.0, the temperature within a range of from about 15° C. to about 30° C., and continuing the initial phase of said first stage operation over a period of time ranging from about 5 to about 30 hours,
adding, at the end of this time period, an additional single charge of sucrose to raise the final sucrose concentration to a level ranging from about 5 percent to about 50 percent, based on the weight of the fermentation medium,
increasing, to begin a second stage operation, the temperature within a range of from about 25° C. to about 35° C., sufficient to increase the rate of activity of the dextranase, and
continuing said second stage operation at said temperature over an additional period ranging from about 12 hours to about 48 hours, sufficient to produce dextran polymer of said controlled number average molecular weight, and molecular size distribution.

12. The process of claim 11 wherein the *Leuconostoc mesenteroides* is a microorganism having all of the identifying characteristics of *Leuconostoc mesenteroides* ATCC 10830.

13. The process of claim 11 wherein each of the microorganisms of the mixture is obtained from a fermentation medium wherein the respective microorganism is grown to a stationary phase prior to their addition to the production fermentation reaction zone.

14. The process of claim 11 wherein during the initial stage of the operation the sucrose concentration level maintained in said production fermentation zone ranges from about 1.5 percent to about 2.5 percent, the pH ranges from about 5.4 to about 6.0, the temperature from about 25° C. to about 28° C., and the first stage operation is continued during the initial phase of said first stage operation is continued over a period ranging from about 10 hours to about 25 hours,
the single charge of sucrose added to the production fermentation zone at the end of this period ranges from about 10 percent to about 30 percent,
the temperature of the second stage of the operation is increased within a range of from about 28° C. to about 30° C., and
the second stage of operation is continued over a period of time ranging from about 32 hours to about 38 hours.

15. The process of claim 11 wherein the number average molecular weight of the dextran polymer ranges from about 70,000 to about 75,000, and has a polydispersity index of about 1.

16. The process of claim 15 wherein the dextran polymer is of high purity and suitable as a blood plasma, or blood plasma extender after isolation from the production fermentation reaction zone.

17. The process of claim 11 wherein the number of stages employed to conduct the operation is greater than 2.

18. The process of claim 17 wherein 3 stages are employed to conduct the operation.

19. The process of claim 11 wherein the dextran polymer that is produced is of number average molecular weight ranging from about 40,000 to about 150,000, and has a polydispersity index of about 1.

* * * * *